(12) United States Patent
Borut et al.

(10) Patent No.: US 8,604,194 B2
(45) Date of Patent: Dec. 10, 2013

(54) SALTS OF O-DESMETHYL-VENLAFAXINE

(75) Inventors: Furlan Borut, Ljubljana (SI); Anton Copar, Ljubljana (SI)

(73) Assignee: Lek Pharmaceuticals D.D., Ljubljana (SI)

( * ) Notice: Subject to any disclaimer, the term of this patent is extended or adjusted under 35 U.S.C. 154(b) by 464 days.

(21) Appl. No.: 12/865,348

(22) PCT Filed: Jan. 29, 2009

(86) PCT No.: PCT/EP2009/050987
§ 371 (c)(1),
(2), (4) Date: Dec. 28, 2010

(87) PCT Pub. No.: WO2009/095431
PCT Pub. Date: Aug. 6, 2009

(65) Prior Publication Data
US 2011/0082213 A1    Apr. 7, 2011

(30) Foreign Application Priority Data

Jan. 29, 2008 (EP) .................................. 08150802

(51) Int. Cl.
*C07D 239/22* (2006.01)
(52) U.S. Cl.
USPC ....................................................... 544/314
(58) Field of Classification Search
CPC ................................................. C07D 239/557
See application file for complete search history.

(56) References Cited

U.S. PATENT DOCUMENTS 6,673,838 B2    1/2004    Hadfield et al.

FOREIGN PATENT DOCUMENTS

| CN | 101 074 200 | A | | 11/2007 |
| CN | 101074200 | A | | 11/2007 |
| CN | 101 081 816 | A | | 12/2007 |
| CN | 101081816 | A | * | 12/2007 |
| EP | 0 112 669 | A2 | | 7/1984 |
| WO | WO-00/32555 | A | | 6/2000 |
| WO | WO-02/064543 | A | | 8/2002 |
| WO | WO-03/103603 | A | | 12/2003 |
| WO | WO-2007/030537 | A | | 3/2007 |
| WO | WO 2007/120925 | A2 | | 10/2007 |

OTHER PUBLICATIONS

Stahl et al, Handbook of Pharmaceutical Salts: Properties, Selection and Use, 2002, Wiley—VCH, 2002, pp. 340-341.*
Kling et al, Journal of Pharmacy and Pharmacology, Rat Brain and Serum Lithium Concentrations After Acute Injections of Lithium Carbonate and Orotate, 1978, 30, pp. 368-370.*
B Vitamins (Wickipedia, retrieved from internet on Jun. 11, 2013 from http://en.wikipedia.org/wiki/B_vitamins).*
Yardley et al., 2-Phenyl-2-(1-hydroxycycloalkyl) ethylamine Derivatives: Synthesis and Antidepressant Activity, J. Med. Chem., 33 (10), 1990, pp. 2899-2905.
Fusao Takusagawa et al, The Crystal Structure of Orotic Acid Monohydrate (Vitamin $B_{13}$), Bulletin of the Chemical Society of Japan, vol. 46, pp. 2011-2019 (1973).
Extract from Scifinder: Cas Registry No. 65-86-1.

* cited by examiner

*Primary Examiner* — Paul A Zucker
(74) *Attorney, Agent, or Firm* — Arent Fox LLP

(57) ABSTRACT

Novel pharmaceutically acceptable salts of desvenlafaxine with physiologically ubiquitous ions selected from sugar acids and vitamins, processes for their preparation, pharmaceutical compositions containing them and uses therefor are described.

2 Claims, 9 Drawing Sheets

SALTS OF O-DESMETHYL-VENLAFAXINE

CROSS-REFERENCE TO RELATED APPLICATION

Figure 1:
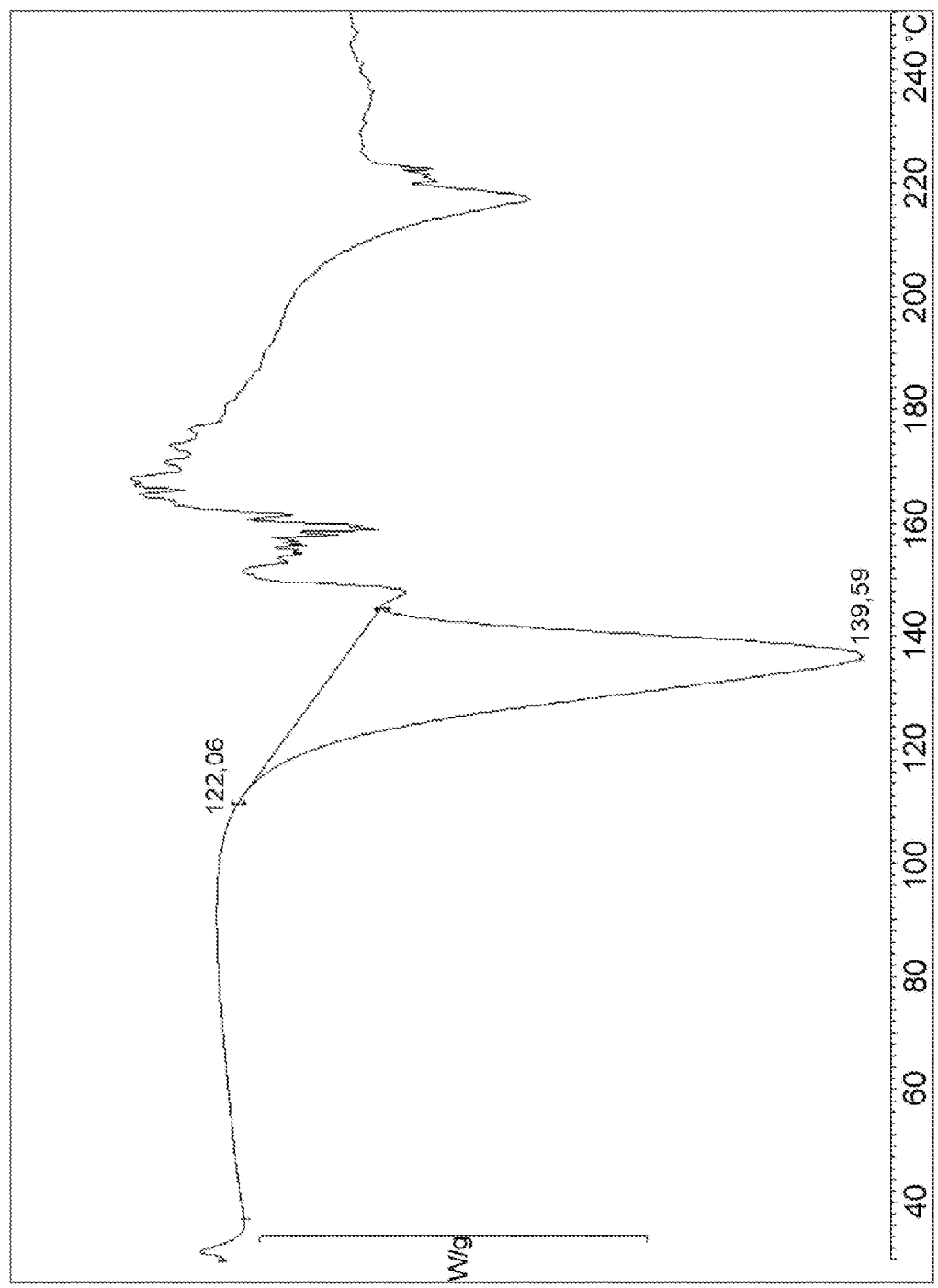

This application is a 371 National Stage entry of International Application No. PCT/EP2009/050987, filed Jan. 29, 2009, now WO 2009/095431 with an International Publication date of Aug. 6, 2009, which claims the benefit of priority to EP 08150802.0, filed Jan. 29, 2008, the entire specification, claims and drawings of which are incorporated herewith by reference.

The present invention relates to novel pharmaceutically acceptable salts of desvenlafaxine, to processes for their preparation, to pharmaceutical compositions containing them and to the use thereof.

The compound 1-(2-dimethylamino-1-(4-hydroxyphenyl)ethyl)cyclohexanol (Formula 1), generically named O-desmethyl-venlafaxine or desvenlafaxine is the major metabolite of venlafaxine and has been shown to inhibit noradrenaline and serotonine uptake. Its preparation was first disclosed in J. Med. Chem. 1990, 33, pp 2899 in a form of fumarate salt.

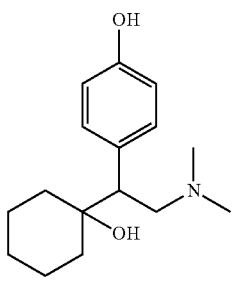

Formula 1

Physical properties of solid pharmaceutical ingredients are essential for preparation of pharmaceutical compositions and its bioavailability. Salts often improve biological characteristics of mother compounds without modifying of primary pharmacological activity, based on mechanism of action. Contrary to the disclosure of EP 0 112 669 A1 that the pharmaceutically acceptable acid addition salts of 2-phenyl-2-cycloalkenyl-ethylamine derivatives can be formed conventionally by reaction with an equivalent amount of any acid which forms a non-toxic salt, in the case of desvenlafaxine the most of its conventional salts are unsuitable due to inappropriate hygroscopicity, stability, solubility, and physically state or simply they cannot be prepared in reasonable yields or cannot be obtained at all.

As desvenlafaxine fumarate has exhibited unsuitable physicochemical and permeability characteristics better forms of desvenlafaxine might be found. A free base is exemplified in WO 00/32555 and improved by preparation of stable crystalline forms (WO 07/120,925). Two new salts such as succinate WO 02/64543 and formate (WO 03/103603) were also prepared and showed better site-specific absorption.

Additional two salts desvenlafaxine aspartate (CN101074200A) and desvenlafxine tartrate (CN101081816) were also disclosed.

Oral administration of desvenlafaxine can result in incidence of nausea, vomiting, diarrhea, and abdominal pain what is able to be improved by designing special final dosage forms including sustained release oral formulations. A different physico-chemical properties of desvenlafaxine salts can be also preferred for the preparation of sustained release formulation.

Thus there is a continuing need to obtain new salts of desvenlafaxine having improved physical and/or chemical properties.

We have surprisingly found that using physiologically ubiquitous ions selected from the group of amino acids, fatty acids, sugar acids and vitamins form well defined salts of desvenlafaxine with specific physico-chemical properties.

In one aspect the present invention relates to novel salts of desvenlafaxine with physiologically ubiquitous ions (ions which are constitutional parts of human cells and contributes in biochemical pathways) selected from the group of amino acids, fatty acids, sugar acids and vitamins.

In one aspect the present invention relates to hydrates and solvates of salts of desvenlafaxine with physiologically ubiquitous ions selected from the group of amino acids, fatty acids, sugar acids and vitamins.

In one aspect of the invention physiologically ubiquitous ions are selected from amino acids, preferably from dicarboxylic amino acids, most preferably from aspartic and glutamic acid. L-enantiomers or D-enantiomers or racemates are used, but physiological L-aspartic and L-glutamic acid are preferred.

In another aspect of the invention physiologically ubiquitous ions are selected from fatty acids, preferably from mono- and dicarboxylic $C_{10}$-$C_{24}$ saturated or unsaturated aliphatic acids, preferably palmitic and stearic acid are used.

In another aspect of the invention physiologically ubiquitous ions are selected from sugar acids, preferably selected from hexuronic, hexonic and hexaric acids, most preferably glucuronic acid is used. Physiological D-enantiomer (Formula 2) is preferred.

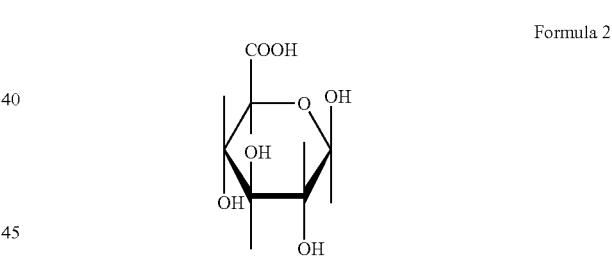

Formula 2

In another aspect the present invention relates to desvenlafaxine D-glucuronate.

In another aspect the present invention relates to crystalline desvenlafaxine D-glucuronate.

In another aspect the present invention relates to desvenlafaxine D-glucuronate in amorphous form.

Figure 8:
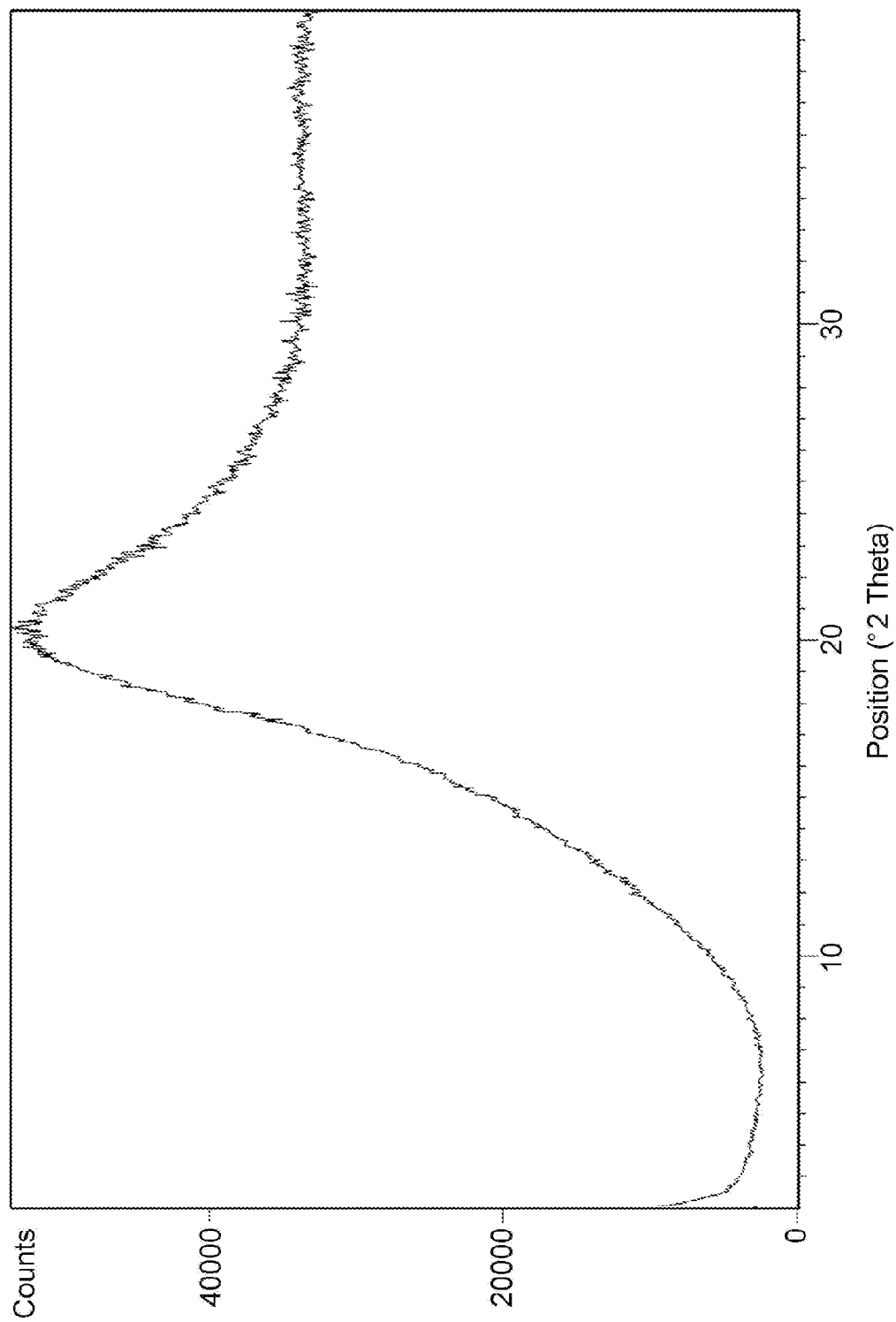

In another aspect the present invention relates to desvenlafaxine D-glucuronate in amorphous form having a powder x-ray diffraction pattern such as in FIG. 8.

In another aspect the present invention relates to desvenlafaxine D-glucuronate hydrates and solvates.

In another aspect the present invention relates to desvenlafaxine D-glucuronate monohydrate.

In another aspect the present invention relates to crystalline desvenlafaxine D-glucuronate monohydrate.

In another aspect the present invention relates to desvenlafaxine D-glucuronate monohydrate, having a powder x-ray diffraction pattern comprising the following characteristic reflection angles 2θ: 4.8±0.2°, 13.5±0.2°, 17.0±0.2°, 21.2±0.2°, 21.8±0.2°, 23.9±0.2° and 25.4±0.2°.

In another aspect the present invention relates to desvenlafaxine D-glucuronate monohydrate, having a powder x-ray diffraction pattern comprising the following characteristic reflection angles 2θ: 4.8±0.2°, 13.5±0.2°, 15.9±0.2°, 17.0±0.2°, 21.2±0.2°, 21.8±0.2°, 23.9±0.2°, 25.4±0.2°, 28.9±0.2° and 31.9±0.2°.

Figure 7:
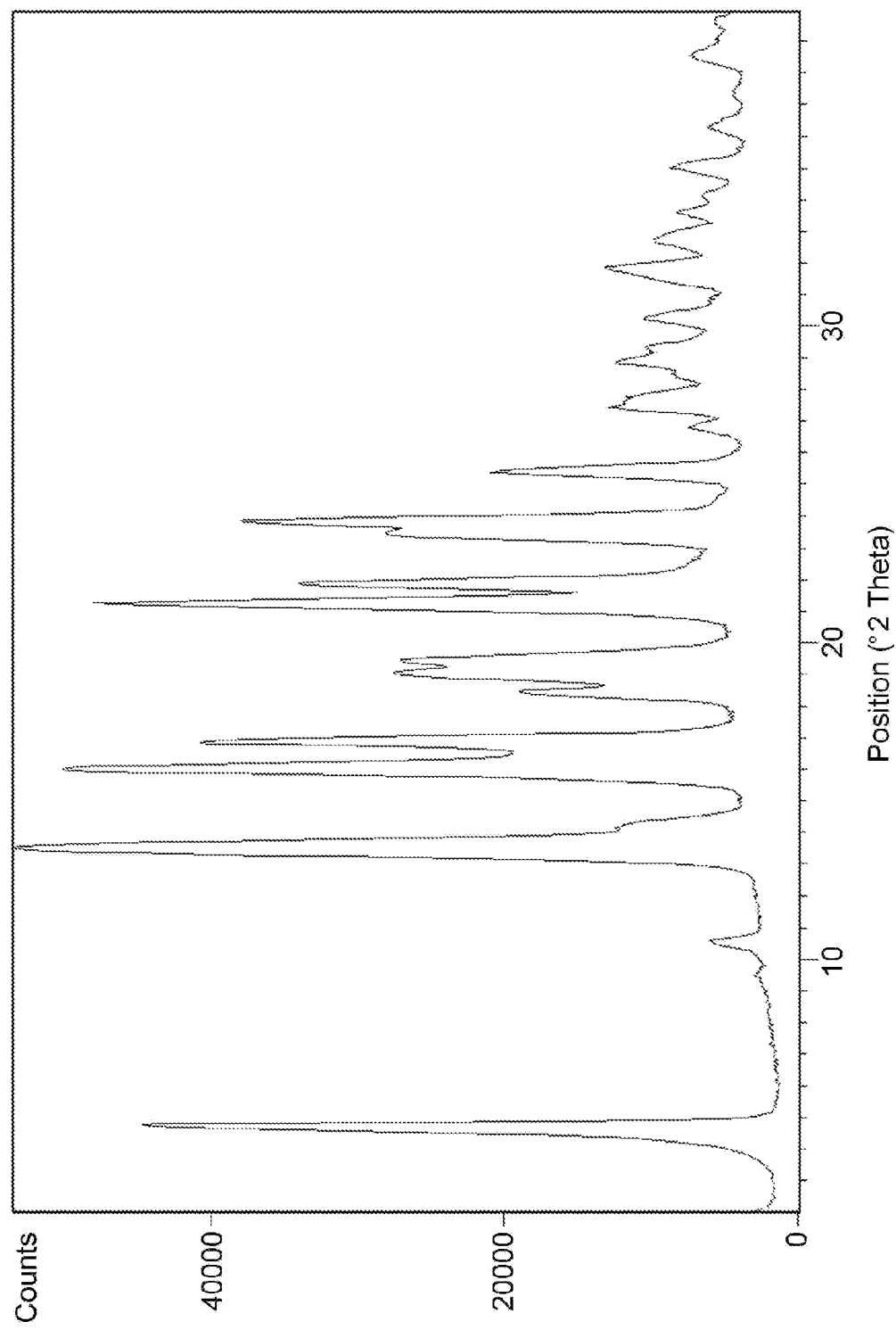

In another aspect the present invention relates to desvenlafaxine D-glucuronate monohydrate, having a powder x-ray diffraction pattern such as in FIG. 7.

In another aspect of the invention physiologically ubiquitous ions are selected from vitamins, preferably from vitamin C (ascorbic acid), or from Vitamin $B_{13}$ (orotic acid), most preferably orotic acid (Formula 3) is used.

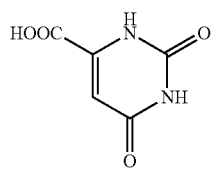

Formula 3

In another aspect the present invention relates to desvenlafaxine orotate.

In another aspect the present invention relates to crystalline desvenlafaxine orotate.

In another aspect the present invention relates to desvenlafaxine orotate Form I, having a powder x-ray diffraction pattern comprising the following characteristic reflection angles 2θ: 5.1±0.2°, 13.9±0.2°, 15.4±0.2°, 17.6±0.2°, 20.0±0.2° and 26.1±0.2°.

In another aspect the present invention relates to desvenlafaxine orotate Form I, having a powder x-ray diffraction pattern comprising the following characteristic reflection angles 2θ: 5.1±0.2°, 6.5±0.2°, 12.1±0.2°, 13.0±0.2°, 13.9±0.2°, 15.4±0.2°, 17.6±0.2°, 20.0±0.2° and 26.1±0.2°.

Figure 9:
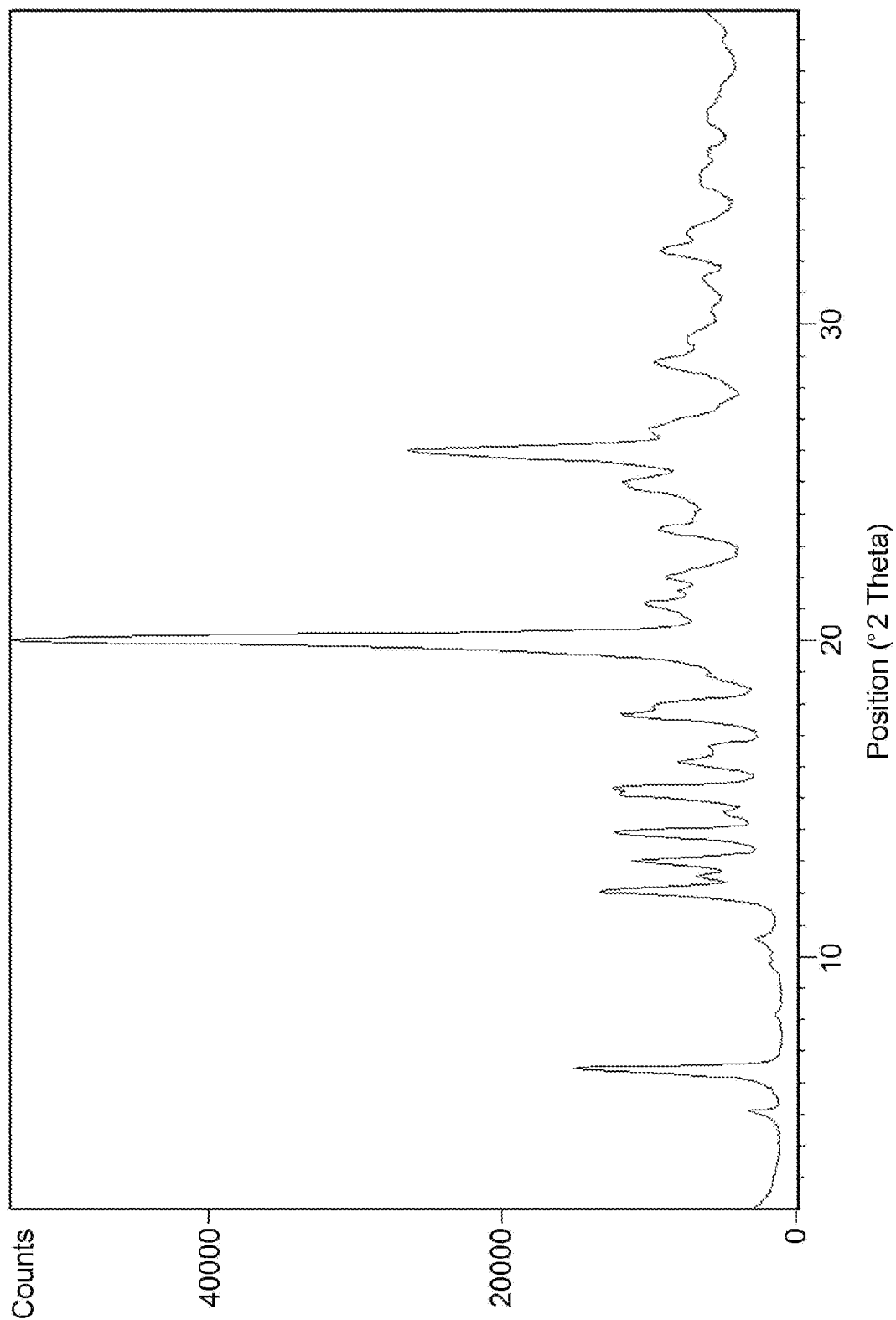

In another aspect the present invention relates to desvenlafaxine orotate Form I, having a powder x-ray diffraction pattern such as in FIG. 9

In another aspect the present invention relates to desvenlafaxine orotate in amorphous form.

In another aspect the present invention relates to desvenlafaxine orotate hydrates and solvates.

In another aspect the present invention relates to a process of preparing salts of desvenlafaxine with physiologically ubiquitous ions selected from the group of amino acids, fatty acids, sugar acids and vitamins by providing a mixture of desvenlafaxine base and physiologically ubiquitous ions selected from the group of amino acids, fatty acids, sugar acids and vitamins respectively in a suitable solvent system, comprised of a single solvent or a mixture of solvents, and isolating the obtained desvenlafaxine salt by precipitation, filtration of the solid salt, evaporation, spray drying or other conventional techniques known in the art.

Suitable solvents are solvents of medium polarity, selected from alcohols, ketones, nitriles, and esters or mixtures thereof, preferably selected from acetone, $C_1$-$C_4$ alcohols, acetonitrile and ethyl acetate.

Physiologically ubiquitous acid in natural state or in solution can be added to the solution of desvenlafaxine base.

The physiologically ubiquitous acid is added in an equimolar ratio to desvenlafaxine base or an excess of the acid is used. A molar ratio of the physiologically ubiquitous acid to desvenlafaxine base is preferably 1.2:1, more preferably 1.05:1.

The temperature of solvent system comprising a mixture of desvenlafaxine base and physiologically ubiquitous acid is from ambient temperature to the boiling point of the solvent system, preferably at elevated temperature below the boiling point or at the boiling point under reflux.

Desvenlafaxine salt can be isolated or recovered from the reaction solution by precipitation. The precipitation can be spontaneous depending on solvent system. Alternatively, the precipitation can be induced by reducing the temperature of reaction mixture, especially if initial temperature of reaction mixture is elevated. The precipitation can also be induced by reduction of solution volume, preferably under diminished pressure, or by complete evaporation of solvent. Furthermore, the precipitation my be caused by adding an antisolvent, e.g. water, ethers and hydrocarbons.

In one aspect of the invention desvenlafaxine salt compositions are prepared by adding physiologically ubiquitous acid in natural state or in solution to the solution of desvenlafaxine in a solvent of medium polarity, selected from alcohols, ketones, nitriles, and esters or mixtures thereof, preferably selected from acetone, $C_1$-$C_4$ alcohols, acetonitrile and ethyl acetate, optionally heating the mixture to obtain a solution and cooling. The precipitation of salt occurs after long standing the solution at appropriate bellow 50° C., preferably between −20 to 25° C., after cooling the stirred mixture from heated solution bellow 50° C., preferably to room temperature or bellow, both after optional concentration of the solution by partial evaporation of solvents.

In another option the salt is formed by reprecipitation in a suspension of one or both starting components, or by precipitation adding antisolvent preferably selected from water, ethers and hydrocarbons, most preferably from water and diethyl ether.

In another aspect of the invention desvenlafaxine salt compositions are prepared by adding physiologically ubiquitous acid in natural state or dissolved to a solution of desvenlafaxine base in lower alcohol preferably methanol or ethanol following by complete or partial evaporation of the solvents.

In another aspect of the present invention desvenlafaxine D-glucuronate is prepared by adding D-glucuronic acid in solid state to the solution of desvenlafaxine in a solvent of medium polarity, selected from alcohols, ketones, nitriles, and esters, preferably selected from acetone, C1-C4 alcohols, acetonitrile and ethyl acetate, optionally heating the mixture to obtain a solution and cooling. The precipitation of salt occurs after long standing the solution at appropriate bellow 50° C., preferably between −20 to 25° C., after cooling the stirred mixture from heated solution bellow 50° C., preferably to room temperature or bellow, both after optional concentration of the solution by partial evaporation of solvents. In another option the salt is formed by reprecipitation in a suspension of one or both starting components, or by precipitation adding antisolvent preferably selected from water, ethers and hydrocarbons, most preferably from water and diethyl ether.

In another aspect of the present invention desvenlafaxine glucuronate is prepared by adding glucuronic acid, preferably D-glucuronic acid (to obtain D-glucuronate), in a solid state to a solution of desvenlafaxine base in lower alcohol preferably methanol or ethanol following by complete or partial evaporation of the solvents.

In one preferred example desvenlafaxine base is dissolved in a boiling acetone—water mixture. D-glucuronic acid in a solid state is added to the solution of desvenlafaxine base. The obtained precipitate is filtered and dried under vacuum.

Desvenlafaxine D-glucuronate prepared according to such procedure exhibits melting point at 120.5 to 131.5, preferably 121° C.

Figure 2:
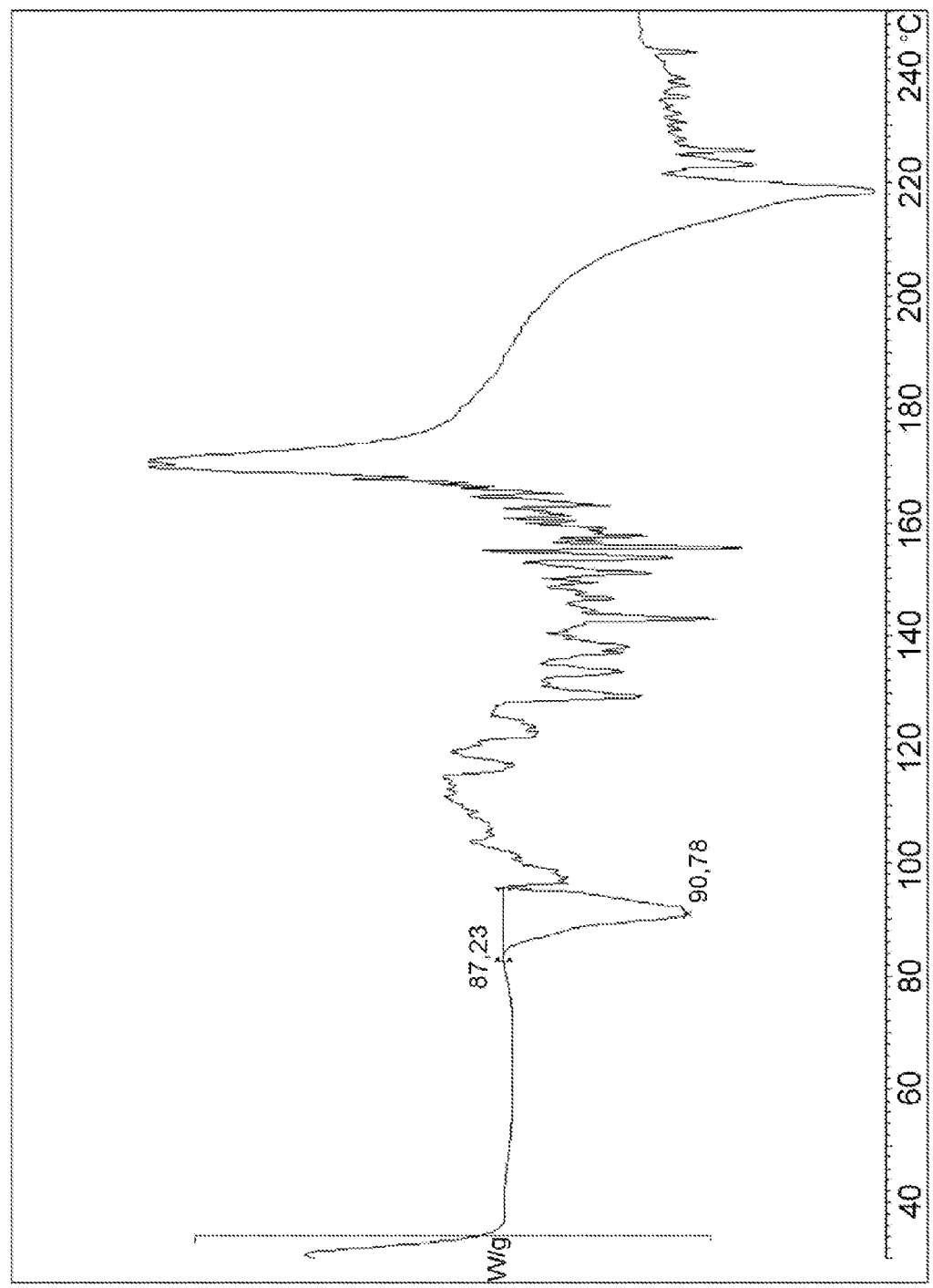

Desvenlafaxine D-glucuronate prepared according to such procedure exhibits the IR spectrum as shown in the FIG. 2

Desvenlafaxine D-glucuronate prepared according to such procedure is crystalline and contains 3-4% of water what corresponds to monohydrate. It is characterized by X-ray powder diffraction pattern such as in FIG. 7 comprising peaks at about: 4.8; 13.5; 15.9; 17.0; 21.2; 21.8; 23.9; 25.4; 28.9; 31.9° Theta.

In another preferred example desvenlafaxine base is dissolved in a lower boiling alcohol, preferably C2-C3 alcohol, most preferably isopropanol. D-glucuronic acid in a solid state is added to the solution of desvenlafaxine base. The product is obtained after adding diethyl ether and cooling to the room temperature.

Desvenlafaxine D-glucuronate prepared according to such procedure contains only moisture water (assay bellow 1.2%) and is amorphous. It exhibits melting point at around 85° C.C (with decomposition).

Figure 5:
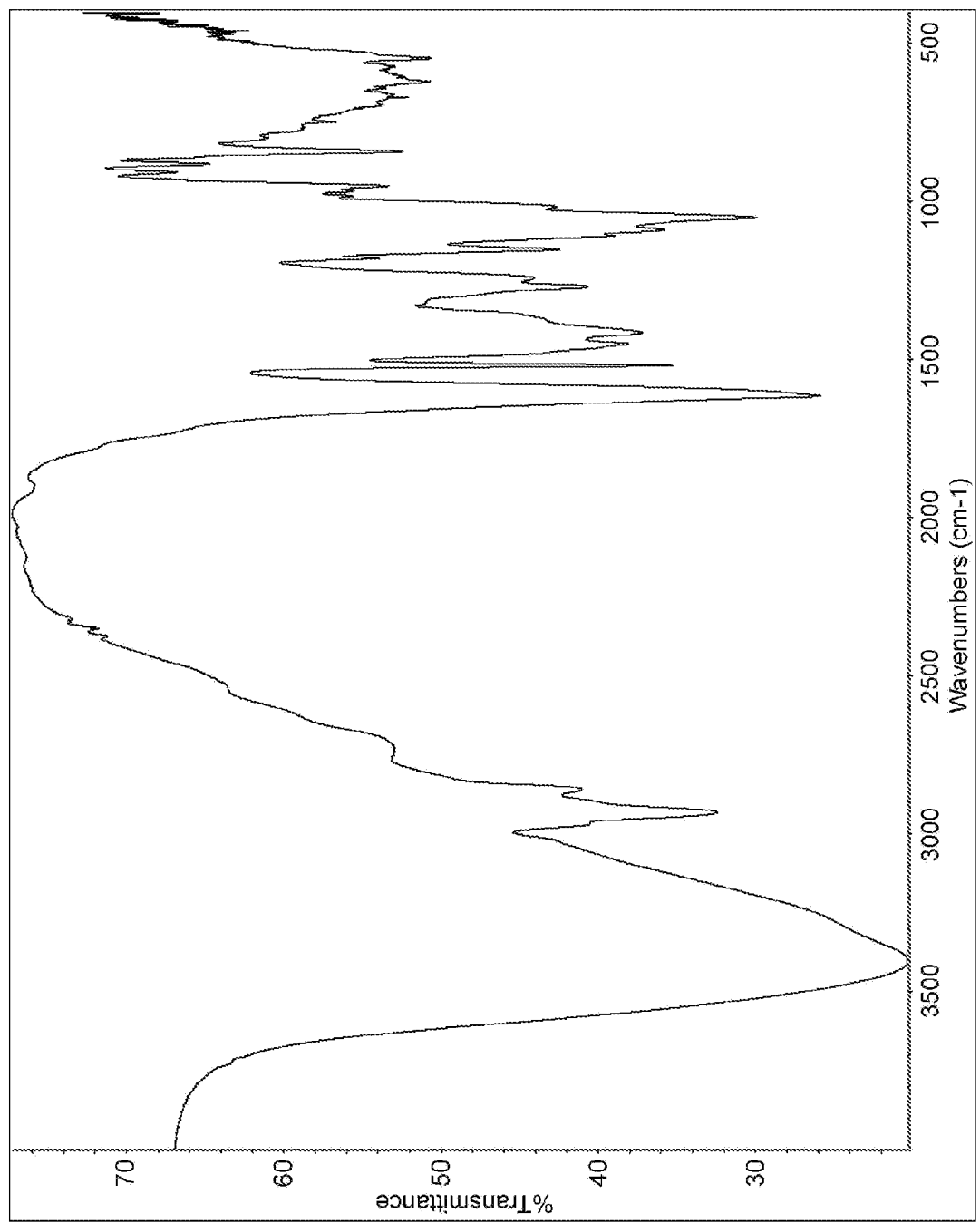

Desvenlafaxine D-glucuronate prepared according to such procedure exhibits the IR spectrum as shown in the FIG. 5.

Desvenlafaxine D-glucuronate prepared according to such procedure are characterized by X-ray powder diffraction and shows no peaks.

In another aspect of the present invention desvenlafaxine base is dissolved in a boiling lower alcohol, preferably ethanol. Orotic acid in a solid state is added to the solution of desvenlafaxine base. The product is obtained after adding diethyl ether and cooling down to 0° C.

Desvenlafaxine orotate prepared according to such procedure exhibits melting point 144 to 154° C., preferably 148.5° C.

Desvenlafaxine orotate prepared according to such procedure exhibits the IR spectrum as shown in the FIG. 8

Desvenlafaxine orotate prepared according to such procedure is crystalline and is characterized by X-ray powder diffraction pattern such as in FIG. 9 comprising peaks at about 5.1; 6.5; 12.1; 13.0; 13.9; 15.4; 17.6; 20.0; 26.1° Theta.

Another aspect of the present invention is a pharmaceutical composition for administering a therapeutically effective amount of desvenlafaxine salts with physiologically ubiquitous ions of the present invention, preferably desvenlafaxine D-glucuronate or orotate, in unit dosage form with one or more pharmaceutically acceptable carriers or other excipients. O-desmethyl-venlafaxine orotate and glucuronate have useful properties for drug formulation. They have good solubility and good dissolution properties.

A therapeutically effective amount of desvenlafaxine salt of the present invention is amount of salt comprising form 15 to 350 mg of desvenlafaxine base, preferably form 20 to 200 mg of desvenlafaxine base, more preferably form 75 to 150 mg of desvenlafaxine base.

Pharmaceutical composition containing desvenlafaxine salts with physiologically ubiquitous ions of the present invention can be in a form suitable for peroral or parental application and is indicated for example for treating the depression, postmenopausal syndrome, fibromyalgia, and neuropathic pain. Pharmaceutical composition in accordance with present invention can be embodied for example in form of tablet, capsules, pellets, granules and suppositories or their combined forms. Pharmaceutical composition in accordance with present invention can be suitable for immediate release or modified release, preferably sustained release, of desvenlafaxine salts of the present invention. Solid pharmaceutical compositions can be shielded for example coated with aim of increasing peletibility or regulating the disintegration or absorption.

Pharmaceutically acceptable excipients may be selected from the group consisting of binders, diluents, disintegrating agents, stabilizing agents, preservatives, lubricants, fragrances, flavoring agents, sweeteners and other excipients known in the field of the pharmaceutical technology. Preferably, carriers and excipients may be selected from the group consisting of lactose, microcrystalline cellulose, cellulose derivatives, e.g. hydroxypropylcellulose, polyacrylates, calcium carbonate, starch, colloidal silicone dioxide, sodium starch glycolate, talc, magnesium stearate, polyvinylpyrrolidone, polyethylene glycol and other excipients known in the field of the pharmaceutical technology.

Optionally, the pharmaceutical compositions of the invention may be combination products comprising one or more additional pharmaceutically active components in addition to desvenlafaxine salts. Preferably, an additional pharmaceutically active component is venlafaxine.

The pharmaceutical compositions may be prepared by methods known in the field of the pharmaceutical technology.

In one aspect of the present invention is related to the process for the preparation of film coated tablets by direct compression. Desvenlafaxine salt compositions of the present invention, preferably desvenlafaxine D-glucuronate, is mixed with lactose, microcrystalline cellulose, starch and aerosil and mixture is sieved. Magnesium stearate is added and mixed again. Cores with mass of 160 mg are tableted. Cores are coated with suspension comprising following essential ingredients: hydroxy propyl methyl cellulose, hydroxypropyl cellulose, polyethylene glycol and titan dioxide in water or alcohol and polished the film coated tablets with talc.

Different salts and different polymorph forms require different techniques. Pharmaceutical composition comprising desvenlafaxine salts of the invention, preferably desvenlafaxine D-glucuronate can be prepared by other suitable procedures for example by dry granulation or peletization. In order to achieve optimum process parameters particles of an active pharmaceutical ingredient should posses certain desired physical and chemical properties, most importantly appropriate particle size and appropriate bulk and tapped density.

We have discovered that the most suitable particle size of crystalline desvenlafaxine D-glucuronate to be incorporated into pharmaceutical composition using the process of our invention is defined by having more than 90% of the crystalline particles with diameter bellow 300 μm.

In another aspect the present invention relates to a pharmaceutical composition comprising crystalline desvenlafaxine D-glucuronate having more than 90% of the crystalline particles with diameter bellow 300 μm.

Surprisingly it was found that desvenlafaxine salts prepared from sugar acids and vitamins, preferably O-desmethyl-venlafaxine orotate and O-desmethyl-venlafaxine glucuronate, have good solubility in water what is clearly represented in Table 1. Good water solubility is one of the key factors for better bioavailability and good absorption of drug from alimentary tract.

TABLE 1

| Solubility of desvenlafaxine salts in water at 23° C. | |
|---|---|
| DESVENLAFAXINE SALT | mg/ml |
| glucuronate amorphous | 338 |
| glucuronate crystalline | 299 |
| orotate | 30.3 |

TABLE 1-continued

Solubility of desvenlafaxine salts in water at 23° C.

| DESVENLAFAXINE SALT | mg/ml |
|---|---|
| succinate | 29.2 |
| fumarate | 6.8 |

In addition the O-desmethyl-venlafaxine orotate and O-desmethyl-venlafaxine glucuronate salts share a common structural feature of having a relatively bulk salt moiety. Further both the orotate salt partner and the glucuronate salt partner are physiologically highly acceptable.

The further aspect of the present invention is a method for the prevention or treatment of major depression, postmenopausal syndrome, fibromyalgia, anxiety and neuropathic pain, with a medicament by using an effective amount of desvenlafaxine salts according to the present invention, preferably desvenlafaxine D-glucuronate or orotate.

In another aspect the present invention is related to use of desvenlafaxine salts according to the present invention, preferably desvenlafaxine D-glucuronate and desvenlafaxine orotate, for the prevention or treatment of major depression, postmenopausal syndrome, fibromyalgia, anxiety and neuropathic pain.

In another aspect the present invention is related to use of desvenlafaxine salts according to the present invention, preferably desvenlafaxine D-glucuronate and desvenlafaxine orotate, for the preparation of a pharmaceutical composition for use in the prevention or treatment of major depression, postmenopausal syndrome, fibromyalgia, anxiety and neuropathic pain.

FIG. 1: DSC thermogram of crystalline desvenlafaxine D-glucuronate

FIG. 2: DSC thermogram of amorphous desvenlafaxine D-glucuronate

Figure 3:
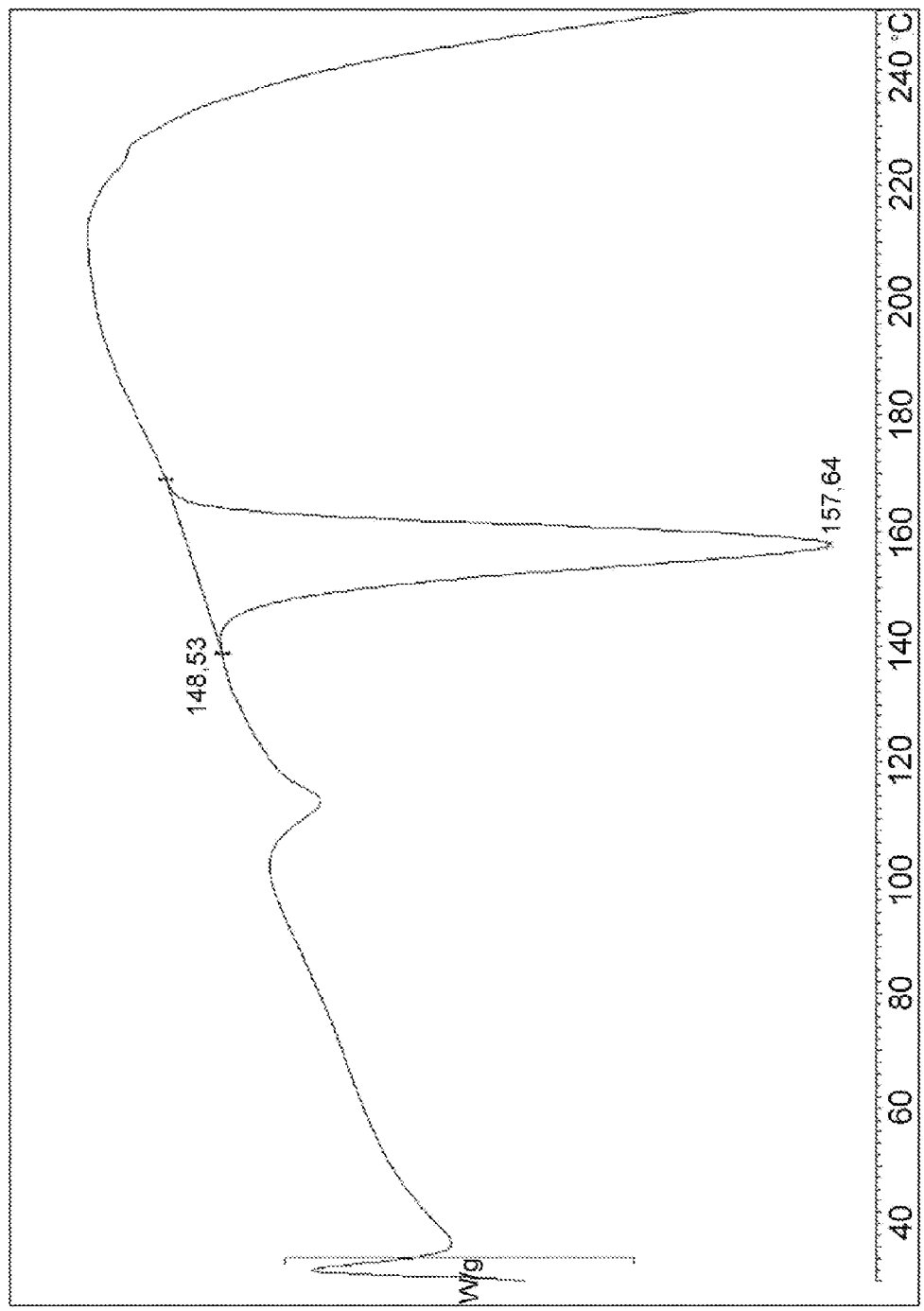

FIG. 3: DSC thermogram of crystalline desvenlafaxine orotate

Figure 4:
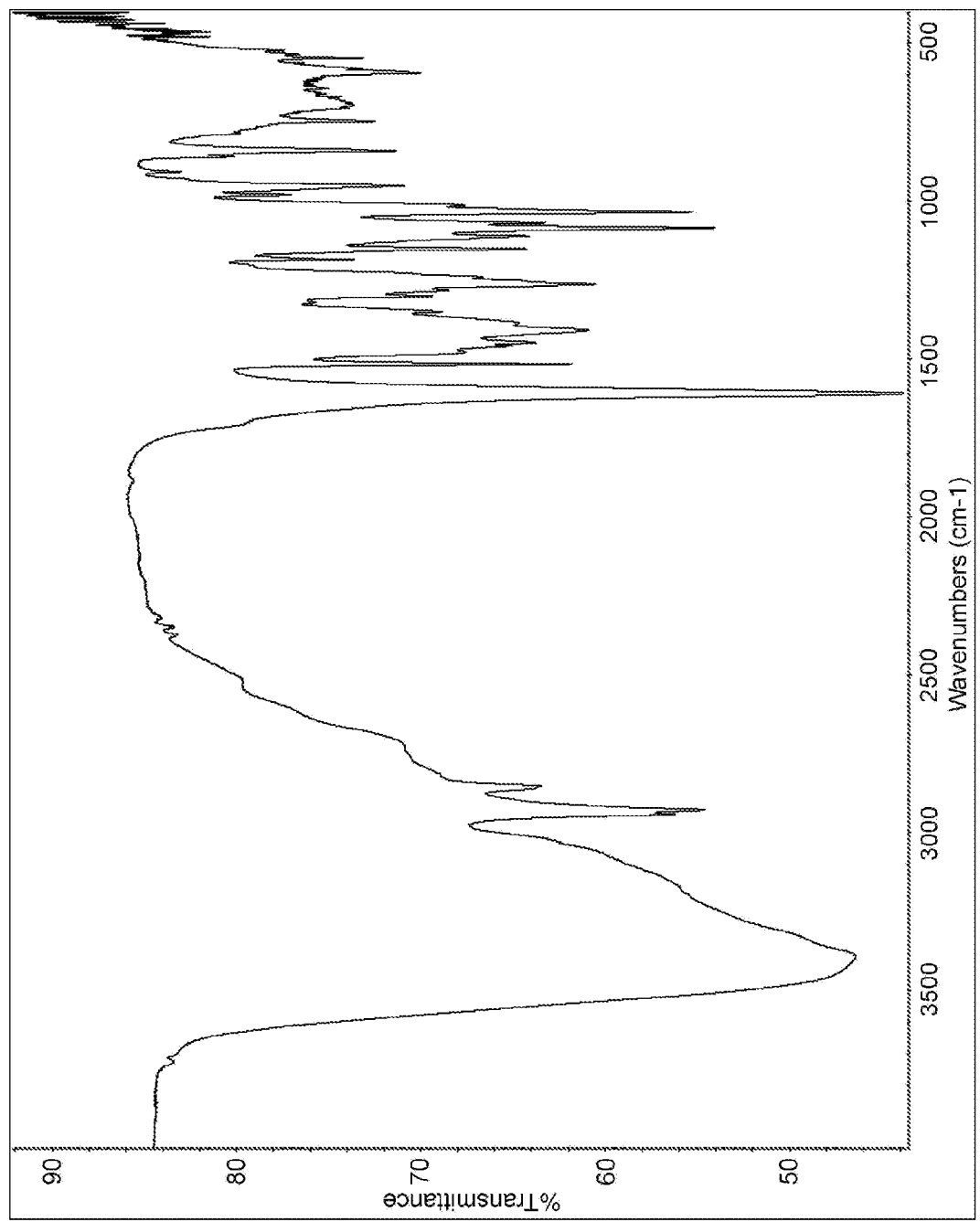

FIG. 4: IR spectrum of crystalline desvenlafaxine D-glucuronate

FIG. 5: IR spectrum of amorphous desvenlafaxine D-glucuronate

Figure 6:
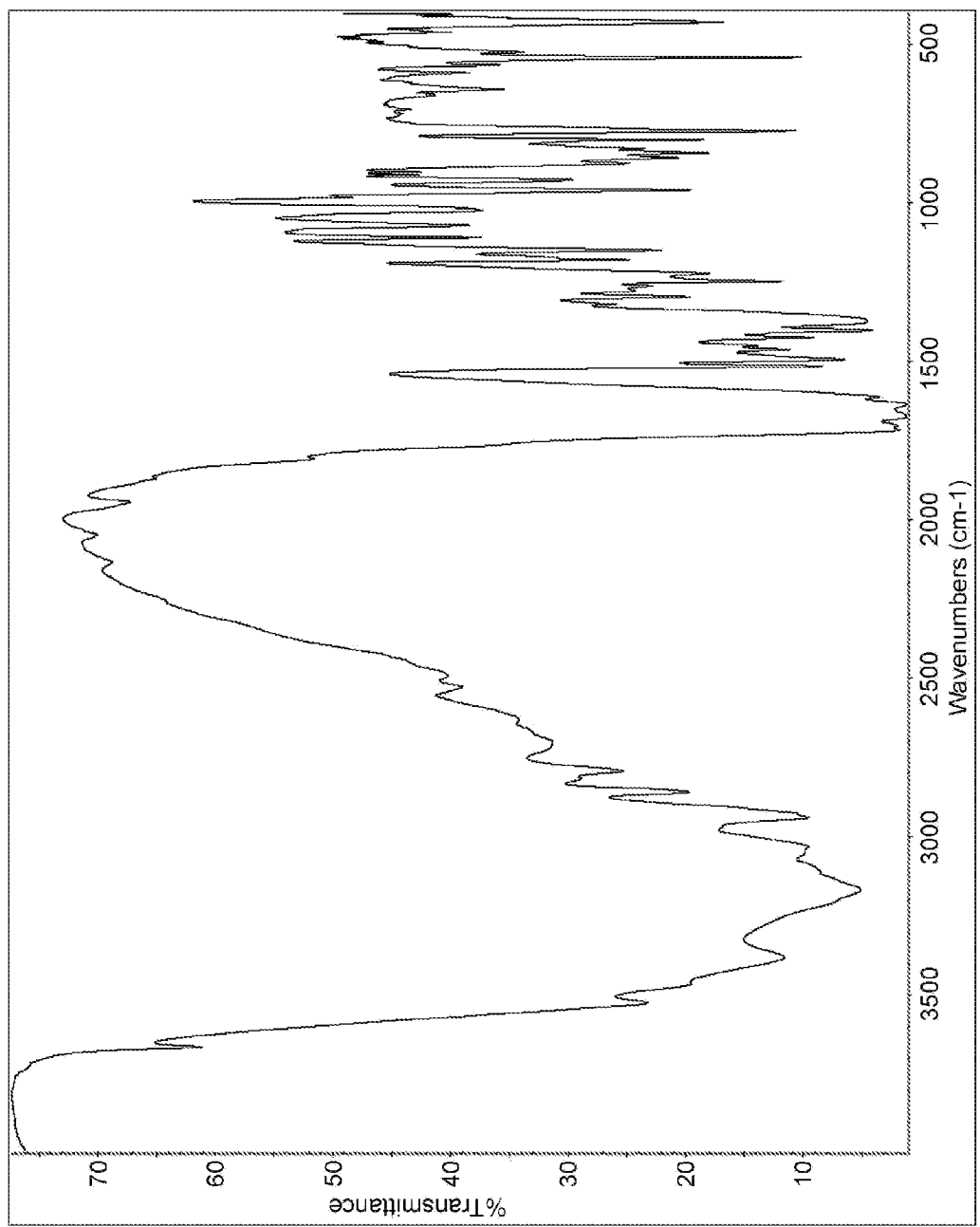

FIG. 6: IR spectrum of crystalline desvenlafaxine orotate

FIG. 7: X-ray powder diffraction pattern of crystalline desvenlafaxine D-glucuronate FIG. 8: X-ray powder diffraction pattern of amorphous desvenlafaxine D-glucuronate FIG. 9: X-ray powder diffraction pattern of crystalline desvenlafaxine orotate The products were analyzed by following methods:

X-Ray Powder Diffraction Method:

Conditions for obtaining powder X-ray diffraction (XRD) patterns: The powder x-ray diffraction patterns were obtained by methods known in the art using Philips X'Pert PRO diffractometer with X'Celerator detector using CuKα radiation (tube operating at 45 kV and 40 mA) in the Bragg-Brentano (reflection) geometry. Data were recorded from 2 to 40° 2θ in steps of 0.033° 2θ and the measurement time of 50 seconds per step. Variable divergence and antiscatter slits were used to maintain 12 mm of sample length irradiated.

IR Spectroscopy Method:

Conditions for obtaining infrared spectra: Fourier transform infrared (FTIR) spectra were recorded with a Nicolet Nexus spectrometer. Spectra over a range of 4000 to 400 cm$^{-1}$ with a resolution of 2 cm$^{-1}$ (16 scans) were recorded on KBr tablets.

Differential Scanning Calorimetry:

Conditions for obtaining DSC thermograms: Thermograms were obtained with Mettler Toledo DSC822$^e$ differential scanning calorimeter. The sample (4-6 mg) was placed in an unsealed aluminium pan with a hole and heated at 5° C./min in the temperature range from 30° C. to 200° C.

EXAMPLE 1

Desvenlafaxine free base may be prepared according to the general procedures of U.S. Pat. No. 6,673,838.

Alternatively desvenlafaxine free base may be prepared from commercial desvenlafaxine succinate. Thus 40.0 g of desvenlafaxine succinate is dissolved in 1000 ml of demineralised water at ambient temperature. 20 ml of 25% ammonia is added at thorough stirring. Soon white precipitate appears and the suspension is further stirred at ambient temperature for one hour. The precipitate is filtered, washed twice with water (2×40 ml) once with acetone (40 ml) and dried under vacuum at 50° C. 25.8 g (93.4%) of pure desvenlafaxine base is obtained.

EXAMPLE 2

2.00 g of desvenlafaxine base is suspended in a mixture of 17.0 ml of acetone and 5.4 ml of demineralised water and heated under reflux conditions. 2.38 g of stearic acid is added and the mixture is further stirred and heated under reflux conditions for 10 minutes, stirred at 30° C. for another 30 minutes and finally stirred at 0° C. for one hour. The product is filtered, washed with mother liquor and dried under vacuum at ambient temperature to yield 3.52 g (84.6%) of stearate salt.

EXAMPLE 3

2.00 g of desvenlafaxine base is dissolved in 50 ml of absolute ethanol at reflux conditions and 1.12 g of L-aspartic acid is added. The solution is further stirred at reflux conditions for 10 minutes and cooled down to −10° C. The mixture is further stirred for one hour at −10° C., the precipitated white crystals are filtered, washed with mother liquor and dried under vacuum at ambient temperature to yield 2.68 g (89.0%) of L-aspartate salt.

EXAMPLE 4

2.00 g of desvenlafaxine base is dissolved in 50 ml of absolute ethanol at reflux conditions and 1.22 g of L-glutamic acid is added. The solution is further stirred at reflux conditions for 10 minutes and cooled down to −10° C. The mixture is further stirred for one hour at −10° C., the precipitated white crystals are filtered, washed with mother liquor and dried under vacuum at ambient temperature to yield 2.78 g (89.2%) of L-glutamic salt.

EXAMPLE 5-a 2.00 g of desvenlafaxine base is suspended in a mixture of 17.0 ml of acetone and 5.4 ml of demineralised water and heated under reflux conditions to obtain clear solution. 1.62 g of D-glucuronic acid is added to the solution, cooled down and stirred further at ambient temperature for 24 hours. The precipitated white crystals are filtered, washed with mother liquor and dried under vacuum at ambient temperature to yield 2.42 g (69.7%) of D-glucuronic salt.

EXAMPLE 5-b 2.00 g of desvenlafaxine base is suspended in 200 ml of acetone and heated under reflux conditions. 1.54 g of D-glucuronic acid and 2 ml of demineralised water is added to the mixture, cooled down and stirred further at ambient temperature for 24 hours. The precipitated white crystals are filtered, washed with mother liquor and dried under vacuum at ambient temperature to yield 3.58 g of D-glucuronic salt, water contain 3.76% (w/w). Yield, calculated to monohydrate is 99%.

EXAMPLE 5-c 2.00 g of desvenlafaxine base is suspended in 70 ml of isopropanol and heated under reflux conditions to obtain clear solution. 1.54 g of D-glucuronic acid is added to the solution, cooled down and stirred further at ambient temperature for 24 hours. The precipitated white crystals are filtered, washed with mother liquor and dried under vacuum at ambient temperature to yield 3.34 g (96.1%) of D-glucuronic salt, water content 0.78%.

EXAMPLE 5-d 2.00 g of desvenlafaxine base is suspended in 50 ml of ethanol and heated under reflux conditions to obtain clear solution. 1.54 g of D-glucuronic acid is added to the solution and cooled down to ambient temperature. 50 ml of diethyl ether is added to the solution and cooled further to 0° C. The suspension is filtered, washed with mother liquor. Slurry-like or foam-like filtered mass is dried under vacuum at ambient temperature to yield amorphous solid 2.46 g (70.8%) of D-glucuronic salt, water contain 1.2%.

EXAMPLE 5-e 2.00 g of desvenlafaxine base is suspended in 360 ml of acetonitrile and heated under reflux conditions to obtain clear solution. 1.54 g of D-glucuronic acid is added to the solution, cooled down and stirred further at ambient temperature for 24 hours. The precipitated solid are filtered, washed with mother liquor and dried under vacuum at ambient temperature to yield 3.18 g of mixture of amorphous desvenlafaxine D-glucuronate and crystalline desvenlafaxine base.

EXAMPLE 6

2.00 g of desvenlafaxine base is suspended in 50 ml of ethanol and heated under reflux conditions to obtain clear solution. 1.30 g of orotic acid is added to the solution and cooled down to ambient temperature. 50 ml of diethyl ether is added to the solution and cooled further to 0° C. The precipitated white crystals are filtered, washed with mother liquor and dried under vacuum at ambient temperature to yield 2.72 g (85.4%) of orotic salt.

The invention claimed is:

1. Desvenlafaxine salts with ions from a vitamin or hydrates or solvates thereof, wherein said vitamin is orotic acid and said desvenlafaxine salt is a crystalline form of desvenlafaxine orotate.

2. Desvenlafaxine orotate according to claim 1 having a powder x-ray diffraction pattern comprising the following characteristic reflection angles 2θ: 5.1±0.2°, 13.9±0.2°, 15.4±0.2°, 17.6±0.2°, 20.0±0.2° and 26.1±0.2°.

* * * * *